US012678002B2

(12) United States Patent
Charbonneau

(10) Patent No.: US 12,678,002 B2
(45) Date of Patent: Jul. 14, 2026

(54) VACUUM EXHAUST DEODORIZER

(71) Applicant: Levi Charbonneau, Ottawa (CA)

(72) Inventor: Levi Charbonneau, Ottawa (CA)

(73) Assignee: Levi Charbonneau, Ottawa (CA)

( * ) Notice: Subject to any disclaimer, the term of this patent is extended or adjusted under 35 U.S.C. 154(b) by 386 days.

(21) Appl. No.: 18/314,941

(22) Filed: May 10, 2023

(65) Prior Publication Data

US 2024/0374093 A1 Nov. 14, 2024

(51) Int. Cl.
*A61L 9/012* (2006.01)
*A47L 7/04* (2006.01)

(52) U.S. Cl.
CPC ................. *A47L 7/04* (2013.01); *A61L 9/012* (2013.01)

(58) Field of Classification Search
CPC .................................. A47L 7/04; A61L 9/012
See application file for complete search history.

(56) References Cited

U.S. PATENT DOCUMENTS

| | | | |
|---|---|---|---|
| 6,231,647 B1 * | 5/2001 | Cheng | A47L 5/24 96/108 |
| 2006/0090290 A1 * | 5/2006 | Lau | A47L 5/24 15/344 |
| 2011/0130877 A1 * | 6/2011 | Lynch | A61L 9/14 239/34 |
| 2015/0202340 A1 * | 7/2015 | Warberg Block | A61L 9/12 239/34 |

* cited by examiner

*Primary Examiner* — Donald R Spamer
(74) *Attorney, Agent, or Firm* — Moffat & Co

(57) ABSTRACT

A vacuum cleaner exhaust deodorizer that is configured to provide aromatic treatment of airflow exiting the exhaust of a vacuum cleaner. The present invention includes a housing wherein the housing includes a plurality of walls defining an interior volume and a shape of the housing. The walls of the housing have formed therein a multitude of apertures. The multitude of apertures permit airflow to penetrate into the interior volume of the housing and interact with a deodorizing compound disposed therein so as to provide aromatic treatment of the airflow as the airflow exits the vacuum exhaust outlet. The housing of the present invention is releasably secured to a door member that is hingedly secured to the vacuum cleaner adjacent the exhaust outlet. The body of the present invention is provided in a shape that is mateably to the shape of the exhaust outlet of the vacuum cleaner.

7 Claims, 2 Drawing Sheets

VACUUM EXHAUST DEODORIZER

FIELD OF THE INVENTION

The present invention relates generally to vacuum cleaner accessories, more specifically but not by way of limitation, a device that is configured to be placed proximate the exhaust outlet of a vacuum cleaner wherein the present invention provides aromatic treatment of the air exiting the exhaust outlet.

BACKGROUND

Carpet is a popular flooring for most residential homes. Carpet material provides a desirable aesthetic appearance and a comfort that many home owners desire. While carpet is desirable, there are many problems that carpet can present to a homeowner. Some studies found that carpeted homes had a greater variety of insects than non-carpeted homes. The studies suggested that most of these insects didn't actually live in the carpeting but once inside the home, many became caught in the carpet pile and perished resulting in the dead insects remaining in the carpet. Carpet also is known to create issues once the carpet becomes wet. The carpet fibers once wet from a glass of water or other fluid can become a breeding ground for mold and mold spores which can create an odor.

On average, individuals shed over a million skin flakes each day. These skin flakes ultimately become wedged into the carpet fibers which will accumulate over time if the carpet is not routinely cleaned. In certain climates and during periods of the year such as fall and spring, the amount of pollen in the air can be significant. While some air filtration is possible of these pollens many can become deposited into the carpet fibers. Lastly, the construction of carpet enables a great deal of dirt retention. Dirt is tracked in on shoes or on the feet and fur of pets. Once dirt gets in the carpet, it creates stains and can increase populations of bacteria, mold, and bugs. All of the aforementioned challenges with carpet can be managed quite easily with routine vacuuming. However, the aforementioned challenges present a common problem for those individuals vacuuming carpet. The mold, dirt and other materials trapped in the carpet produce a undesirable smell emitting from the exhaust flow of the vacuum cleaner.

Accordingly, there is a need for a vacuum cleaner accessory that can be secured to the exhaust of a vacuum cleaner that provides aromatic treatment of the exhaust as it exits the vacuum cleaner.

SUMMARY OF THE INVENTION

It is the object of the present invention to provide a vacuum cleaner exhaust deodorizer that is operable to provide aromatic treatment of the exhaust flow of a vacuum cleaner wherein the present invention includes a body.

Another object of the present invention is to provide a vacuum cleaner accessory that is configured to be placed in the exhaust flow of a vacuum cleaner wherein the body includes a housing.

A further object of the present invention is to provide a vacuum cleaner exhaust deodorizer that is operable to provide aromatic treatment of the exhaust flow of a vacuum cleaner wherein the housing includes an outer wall having a multitude of apertures formed therein.

Yet a further object of the present invention is to provide a vacuum cleaner accessory that is configured to be placed in the exhaust flow of a vacuum cleaner wherein the housing has a deodorizing material disposed therein.

Still another object of the present invention is to provide a vacuum cleaner exhaust deodorizer that is operable to provide aromatic treatment of the exhaust flow of a vacuum cleaner wherein the housing is releasably secured over an exhaust flow opening.

An additional object of the present invention is to provide a vacuum cleaner accessory that is configured to be placed in the exhaust flow of a vacuum cleaner wherein it is contemplated within the scope of the present invention that the housing could be placed in alternate location in the exhaust flow of a vacuum cleaner.

Yet a further object of the present invention is to provide a vacuum cleaner exhaust deodorizer that is operable to provide aromatic treatment of the exhaust flow of a vacuum cleaner wherein the housing is provided in alternate shapes and sizes.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
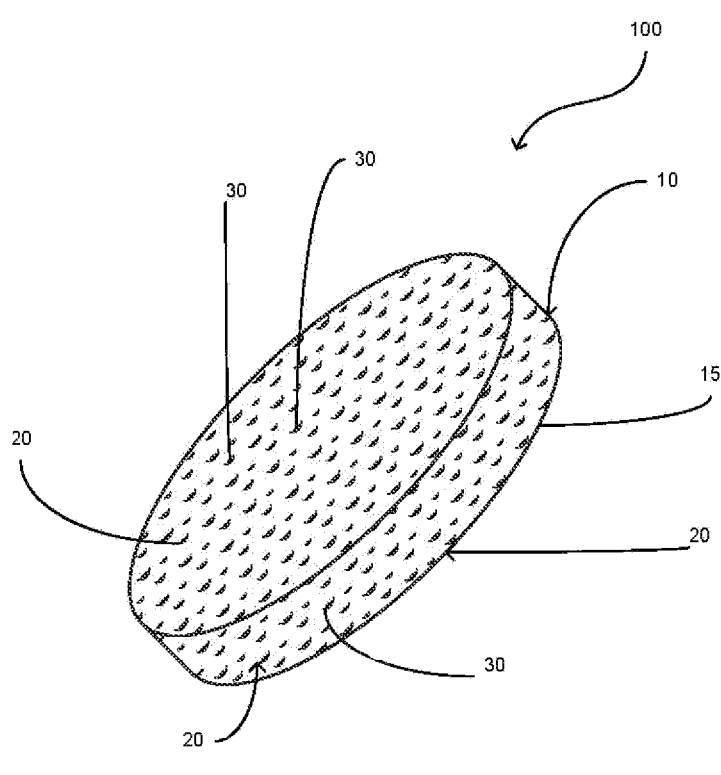
FIG. 1 is a perspective view of the present invention.

Referring now to the drawings submitted herewith, wherein various elements depicted therein are not necessarily drawn to scale and wherein through the views and figures like elements are referenced with identical reference numerals, there is illustrated a vacuum cleaner exhaust deodorizer 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to the Figures submitted herewith, the vacuum cleaner exhaust deodorizer 100 includes a body 10 having a housing 15. The housing 15 includes a plurality of walls 20 and is manufactured from a suitable material such as but not limited to a biodegradable plastic. It is contemplated within the scope of the present invention that the body 10 could be manufactured from a paper-like material wherein this embodiment would be deposited into the vacuum receptacle 98 and provide the functionality of the vacuum cleaner exhaust deodorizer 100 as described herein. The walls 20 include a multitude of apertures 30 wherein the apertures ensure airflow through the housing 15. It is contemplated within the scope of the present invention that the apertures 30 could be provided in alternate shapes, sizes and quantities. The walls 20 of the housing 15 create an interior volume wherein the interior volume has disposed therein a deodorizing compound. While body 10 is illustrated herein as being annular in shape, it is contemplated within the scope of the present invention that the body 10 could be provided in alternate shapes. A preferred embodiment of the vacuum cleaner exhaust deodorizer 100 is to have the body 10 be provided in a shape that is mateable to the shape of the vacuum exhaust outlet 97 of the exemplary vacuum cleaner 99.

Figure 2:
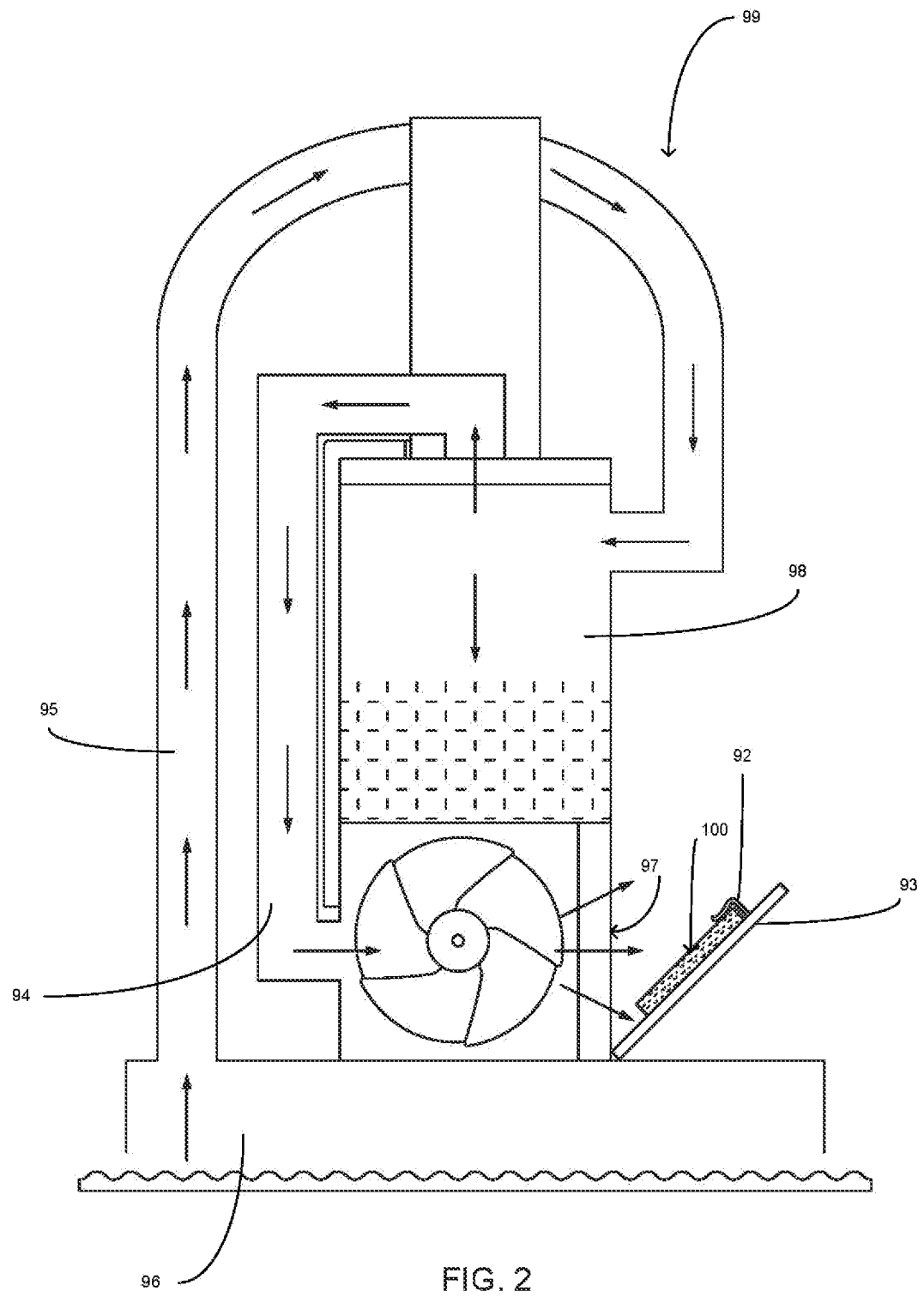
FIG. 2 is an exemplary flow diagram of a vacuum cleaner.

Referring in particular to FIG. 2, an exemplary airflow diagram of the vacuum cleaner 99 is illustrated herein. Air and debris are transferred from the vacuum head 96 through the delivery tube 95 and towards the vacuum receptacle 98. The debris contained in the air is trapped in the vacuum receptacle 98 and the airflow exits the vacuum receptacle 98 out the exhaust tube 94 and is discharged from the vacuum exhaust outlet 97. The vacuum cleaner exhaust deodorizer 100 is releasably secured to a door member 93 with clip 92 wherein the door member 93 is hingedly secured adjacent the vacuum exhaust outlet 97. When the door member 93 is in the closed position the airflow will pass through the apertures 30 formed in the walls 20 and as such be aromatically treated by the deodorizing compound within the interior volume of the housing 15. It is contemplated within the scope of the present invention that the deodorizing compound could be manufactured from alternate materials. By way of example but not limitation, the deodorizing compound could be a fragrance embedded in wax or a gel based material that is configured to be evaporative and provide aromatic treatment of air passing through the housing 15.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A vacuum cleaner exhaust deodorizer configured to provide aromatic treatment of air exiting an exhaust outlet of a vacuum cleaner wherein the vacuum cleaner exhaust deodorizer comprises:

a body, said body having a housing, said housing having a plurality of walls integrally formed wherein the plurality of walls define a shape of the housing, said plurality of walls of said housing having a multitude of apertures formed therein, said multitude of apertures permitting air to flow through said housing, wherein said body is situated adjacent to a door member that forms a part of an outer surface of the vacuum cleaner, said door member being hingedly secured adjacent to an exhaust outlet;

a deodorizing compound, said deodorizing compound being disposed in an interior volume of the housing, said deodorizing compound operable to aromatically treat air flowing through the interior volume of said housing.

2. The vacuum cleaner exhaust deodorizer configured to provide aromatic treatment of air exiting an exhaust outlet of a vacuum cleaner as recited in claim 1, wherein the deodorizing compound is an evaporative gel-based material.

3. The vacuum cleaner exhaust deodorizer configured to provide aromatic treatment of air exiting the exhaust outlet of a vacuum cleaner as recited in claim 2, wherein the body is releasably secured to the door member.

4. The vacuum cleaner exhaust deodorizer configured to provide aromatic treatment of air exiting an exhaust outlet of a vacuum cleaner as recited in claim 3, wherein the housing is mateably shaped to a shape of the exhaust outlet.

5. The vacuum cleaner exhaust deodorizer configured to provide aromatic treatment of air exiting an exhaust outlet of a vacuum cleaner as recited in claim 1, wherein the deodorizing compound is fragrance embedded in a wax.

6. The vacuum cleaner exhaust deodorizer configured to provide aromatic treatment of air exiting an exhaust outlet of a vacuum cleaner as recited in claim 4, wherein the body is placeable in a receptacle inside the vacuum cleaner.

7. The vacuum cleaner exhaust deodorizer configured to provide aromatic treatment of air exiting an exhaust outlet of a vacuum cleaner as recited in claim 6, wherein the housing is manufactured from a biodegradable material.

* * * * *